United States Patent [19]

Lasslo et al.

[11] Patent Number: 4,657,917
[45] Date of Patent: Apr. 14, 1987

[54] PLATELET AGGREGATION INHIBITORY AGENTS

[75] Inventors: Andrew Lasslo, Memphis; Ronald P. Quintana, Germantown; Marion Dugdale, Memphis, all of Tenn.

[73] Assignee: Research Corporation, New York, N.Y.

[21] Appl. No.: 662,533

[22] Filed: Oct. 18, 1984

Related U.S. Application Data

[63] Continuation of Ser. No. 347,037, Feb. 8, 1982, abandoned.

[51] Int. Cl.$^4$ .................. A61K 31/445; A61K 31/44
[52] U.S. Cl. ................................ 514/315; 514/316; 514/330; 514/355
[58] Field of Search ................ 514/315, 316, 330, 355

[56] References Cited

PUBLICATIONS

Lasslo, J. Org. Chem., vol. 22, Jul., (1957), pp. 837–839.
Lasslo, J. Org. Chem., vol. 21, (1956), pp. 958–959.
Beasley, J. Med. Chem., vol. 7, (1964), pp. 698–701.
Quintana, J. Med. Chem., vol. 10, (1967), pp. 1178–1180.
Quintana, J. Pharm., Sci., vol. 52, Dec. 1963, pp. 1186–1188.
Quintana, J. Pharm. Sci., vol. 54, May 1965, pp. 785–787.
Quintana, Throm. Res., vol. 24, (1981), pp. 379–395.
Quintana, Throm. Res., vol. 22, (1981), pp. 665–680.
Quintana, Chem.-Biol. Interactions, vol. 38, (1982), pp. 135–144.
Quintana, Biophys. J., vol. 37, Jan. 1982, pp. 130–133.

*Primary Examiner*—Frederick E. Waddell
*Attorney, Agent, or Firm*—Scully, Scott, Murphy & Presser

[57] ABSTRACT

A pharmaceutical composition in unit dosage form suitable for administration to an animal in need thereof comprising a pharmaceutically acceptable carrier and an amount sufficient to inhibit blood platelet aggregation of a compound selected from the group consisting of:

[A] A compound having the structural formula:

meta- or para-wherein $R_1$ is

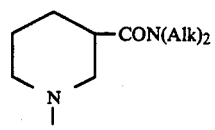

$R_2$ is H or

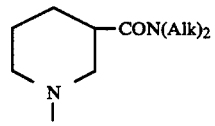

and
Alk is lower alkyl;

[B] A compound having the structural formula:

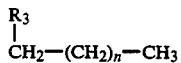

wherein
when $R_3$ is (Abstract continued on next page.)

-continued

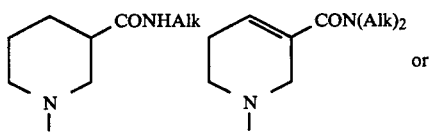

or

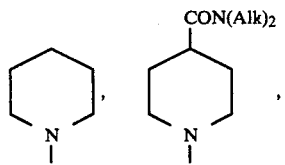

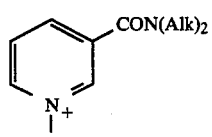

n is 8,
and when $R_3$ is

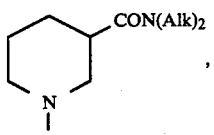

n is 4 or 8, and
Alk is lower alkyl;

[C] A compound having the structural formula:

$$\underset{CH_2}{\overset{R_4}{|}}-(CH_2)_n-\underset{CH_2}{\overset{R_4}{|}}$$

wherein
when $R_4$ is n is 8,
and
when $R_4$ is

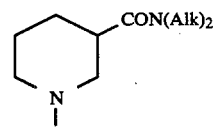

n is 0, 1, 4 or 8, and
Alk is lower alkyl;

[D] A compound having the structural formula:

cis- or trans- 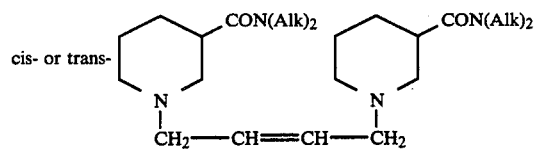

wherein
Alk is lower alkyl; and

[E] Addition salts thereof with pharmaceutically acceptable acids.

22 Claims, 3 Drawing Figures

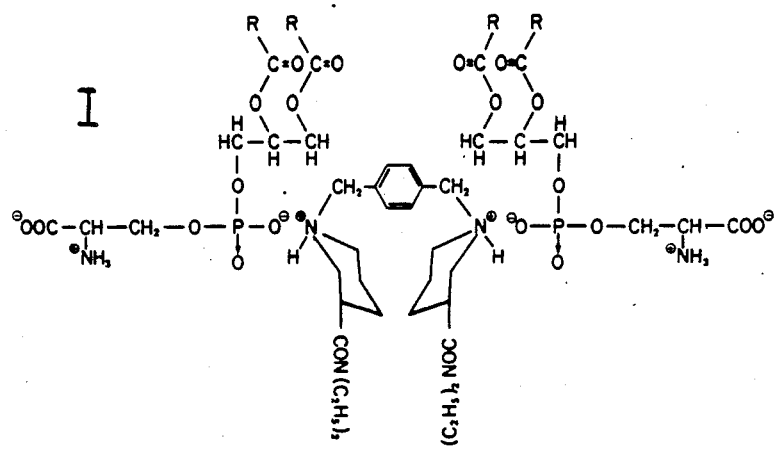
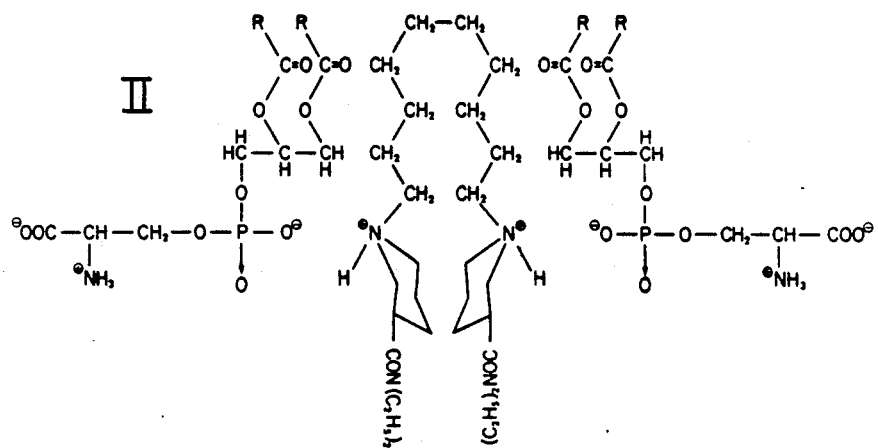
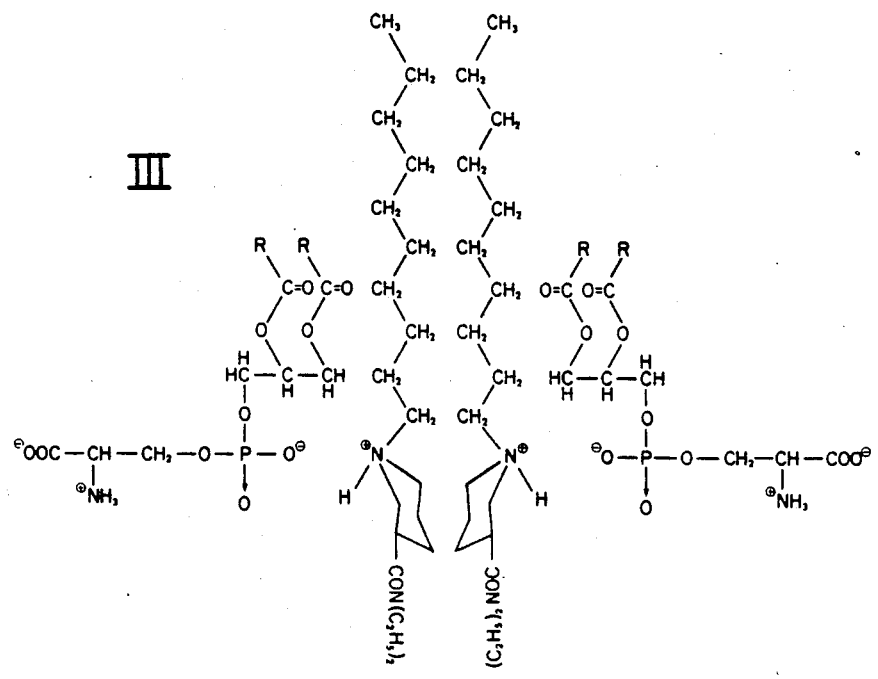

PLATELET AGGREGATION INHIBITORY AGENTS

This is a continuation of co-pending application Ser. No. 347,037 filed 2/8/82 now abandoned.

BACKGROUND OF THE INVENTION

The present invention relates to certain compounds, all useful as platelet aggregation inhibitory agents.

Thromboembolic disorders have been shown to be directly related to the susceptibility of blood platelets to adenosine diphosphate (ADP) induced platelet aggregation, and to other adhesion-release-aggregation chain reactions. Certain animal species wearing prosthetic devices or whose blood is exposed to biomaterials during renal dialysis, blood oxygenation, cardiac catheterization, etc., are especially predisposed to thromboembolic disorders.

The susceptibility of animal blood platelets to aggregation has also been interpreted in terms of platelet membrane stability.

Certain chemical compounds are known to inhibit platelet aggregation. Thus, aspirin, sulfinpyrazone and dipyridamole are known platelet aggregation inhibiting agents. See Quintana et al, *Thromb. Res.*, Vol. 20, pages 405–415 (1980); Cucuianu et al, *J. Lab. Clin. Med.*, Vol. 77, pages 958–974 (1971) and Zucker et al, *J. Lab. Clin. Med.*, Vol. 76, pages 66–75 (1970).

It is an object of the present invention to provide a composition and method for inhibiting blood platelet aggregation thereby being useful for the treatment of thromboembolic disorders.

It is a further object of the present invention to provide a novel class of compounds having platelet aggregation inhibiting activity and platelet membrane stabilization characteristics useful for the treatment of thromboembolic disorders.

SUMMARY OF THE INVENTION

The present invention is predicated on the discovery that compounds of the following structural formulae exhibit blood platelet aggregation inhibiting activity when administered to animals in need thereof:

[A] A compound having the structural formula:

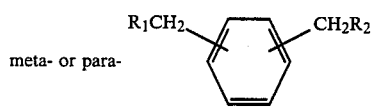

meta- or para-wherein
$R_1$ is

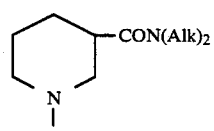

$R_2$ is H or

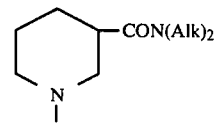

and
Alk is lower alkyl;

[B] A compound having the structural formula:

$$\begin{array}{c} R_3 \\ | \\ CH_2-(CH_2)_n-CH_3 \end{array}$$

wherein
when $R_3$ is

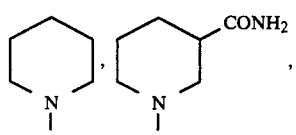

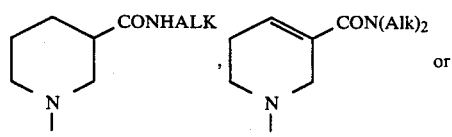

or

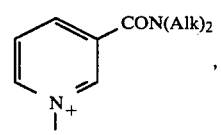

n is 8,
and when $R_3$ is

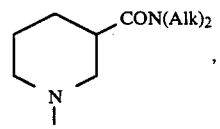

n is 4 or 8, and
Alk is lower alkyl;

[C] A compound having the structural formula:

$$\begin{array}{cc} R_4 & R_4 \\ | & | \\ CH_2-(CH_2)_n-CH_2 \end{array}$$

wherein
when $R_4$ is

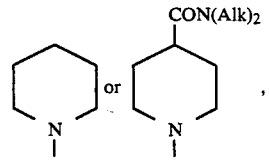

n is 8,
and when R$_4$ is

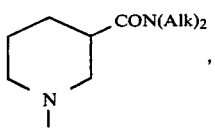

n is 0, 1, 4 or 8, and
Alk is lower alkyl;

[D] A compound having the structural formula:

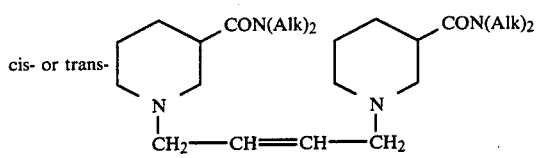

wherein
Alk is lower alkyl; and

[E] Addition salts thereof with pharmaceutically acceptable acids.

The compounds are preferably compounded in unit dosage form with pharmaceutically acceptable carriers such as, e.g., (i) tablets: lactose, starch 5%–acacia 2% in water, corn starch, calcium stearate; (ii) capsules: lactose; (iii) parenterals: sterile solid or constituted aqueous solution, including antibacterial, antioxidant, chelating and buffering agents; (iv) suppositories: cocoa butter, and administered orally, parenterally, or rectally to animals in need thereof.

DESCRIPTION OF THE DRWINGS

FIGS. 1, 2 and 3 depict the structures of three of the platelet aggregation inhibiting compounds of the invention interacting with a monolayer of phosphatidylserine.

DETAILED DESCRIPTION OF THE INVENTION

The bis-substituted derivatives are decidedly more active as platelet inhibiting agents than the mono-substituted compounds. Surprisingly, it has been found that the degree of activity appears to be dependent upon (i) the intra-molecular distances between the ring-nitrogen atoms of the bis-substituted molecule, (ii) planarity and geometric isomerism of the molecules, and (iii) the degree of hydrophobicity. It is theorized that the bis-substituted molecule probably ineracts with two target sites on the platelet surface whenever the intra-molecular distance between the ring-nitrogen atoms corresponds to the distance between the target sites. Thus, those bis-substituted derivatives wherein the intra-molecular distance between the ring-nitrogen atoms is in the range of from about 7.8 to 8.3 Å and, preferably, having a flexibility variance from about 0.1 to about 0.5 Å represent compounds having the highest degree of activity. Thus, although mono-substituted derivatives and bis-substituted derivatives wherein the intra-molecular distances and flexibility variances are outside the ranges set forth above are active platelet aggregation inhibiting agents, the bis-substituted derivatives having the above-noted intra-molecular distance and flexibility variance parameters are the most preferred agents.

It will be understood, however, that steric hindrance factors affect the ability to design platelet aggregation inhibiting molecules conforming to the above generic structural formulae and having the preferred intra-molecular distances and flexibility variance.

The platelet aggregation inhibiting activity of the compounds according to the invention is dependent upon their ability to stabilize the platelet membranes. Membrane stability is, in turn, dependent upon the ability of the inhibitor molecule to penetrate the lipid bilayer of the platelet plasma membrane but retain their ability to subsequently generate sufficient quantities of cationic species to counteract ADP or other stimulus-induced mobilization of calcium ions and thereby restrain or completely inhibit calcium ion dependent phospholipase activity. By so functioning, the agents serve as membrane stabilizing agents.

Thus, the compounds of the invention apparently function by penetrating the lipid bilayer of the platelet membrane and by interacting, as cations, with negatively charged phospholipids (e.g., phosphatidylserine and phosphatidylinositol) within the bilayer's inner segment. As a result of such penetration and interaction, it is theorized that the cations interfere with phospholipase activation by counteracting stimulus-induced mobilization of Ca++ ions and Ca++ − dependent phospholipase activity thereby rendering the platelets less susceptible to aggregation reactions.

Phospholipid layer penetration is characteristic of hydrophobic compounds. Thus, compounds according to the above generic structural formulae appear to interact with a monolayer of phosphatidylserine as follows. (Quintana et al, Interaction of Human Blood Platelet Aggregation Inhibitors with Phospholipid Films, *Thromb. Res.*, Vol. 24, pages 379–395 (1981) Quintana et al, Surface Activity and Human Blood Platelet Aggregation-Inhibitory Potency, *Chem.-Biol. Interactions*, Vol. 38, pages 135–144 (1982). The three compounds:

1,4-Xylylenebis[3-(N,N-diethylcarbamoyl)piperidine Hydrobromide], 1,10-Bis[3-(N,N-diethylcarbamoyl)piperidino]decane Dihydrobromide, and 1-Decyl-3-(N,N-diethylcarbamoyl)piperidine Hydrobromide have the structures depicted in FIGS. 1, 2 and 3, respectively.

While the rigidity of the phenylene moiety would restrain 1,4-xylylenebis[3-(N,N-diethylcarbamoyl)-piperidine hydrobromide] to the head-group region of the film, 1,10-bis[3-(N,N-diethylcarbamoyl)piperidino]-decane dihydrobromide, by the buckling of its flexible decamethylene link, could protrude into the hydrophobic region of the film's fatty acid hydrocarbons; and 1-decyl-3-(N,N-diethylcarbamoyl)piperidine hydrobromide could actually penetrate quite deeply, interlinking its hydrocarbon radical with those of these fatty acids. All three compounds were decidedly platelet aggregation inhibitors and interacted strongly with phospholipid monolayers.

Conversely, the short ethylene linkage would severely constrain 1,2-bis[3-(N,N-diethylcarbamoyl)-piperidino]ethane dihydrobromide from comparable interaction, and the short aliphatic substituent of 1-ethyl-3-(N,N-diethylcarbamoyl)piperidine hydrobromide would preclude its significant penetration into the hydrophobic region. Neither compound could be expected to affect meaningfully surface pressure values or tangibly inhibit platelet aggregation. Experiments verified these conclusions.

The activity of the compounds is also dependent upon the charge level of the ring-nitrogen. The charge on the ring-nitrogen affects the hydrophobicity of the compound thereby directly affecting the aggregation inhibitory potency of the molecule.

For example, the lack of blood platelet aggregation inhibitory activity by 1,4-xylylenebis[3-(N,N-diethylcarbamoyl)pyridinium bromide], 1,10-bis(pyridinium)-decane dibromide and the substantially reduced activity of 1-decyl-3-(N,N-diethylcarbamoyl)pyridinium bromide could be attributed (i) to the aromatic character of the ring structure or (ii) to the charge level of the ring-nitrogen, or (iii) to both. Each factor individually, or both in combination, could lessen hydrophobicity and, as evidenced, reduce aggregation inhibitory potency. Yet, it may be of dominant significance that, as quaternary amines, the heterocyclic nitrogens in the referenced compounds retain the same charge regardless of their environment and consequently, in a biosystem, their hydrophobicity does not even approximate that of corresponding tertiary amines which are generally subject to broad variances in protonation contingent upon the pH of the medium and the specific compounds' $pK_a$ values. This very trait of tertiary amines in the active compounds of the invention (e.g., 1,4-xylylene-bis[3-(N,N-diethylcarbamoyl)piperidine hydrobromide], 1,10-bis[3-(N,N-diethylcarbamoyl)piperidino]decane dihydrobromide, etc.) provides appropriate hydrophobic character for their penetration of the platelet membrane's lipid bilayer without interfering with the subsequent generation of adequate cationic species.

As above noted, compounds of the structural formulae set forth are known in the art although their platelet aggregation inhibiting activity has been heretofore unknown. These known compounds may be prepared according to the methods described in the following publications: Lasslo et al, 3-(N,N-Dialkylcarboxamido)-piperidinoalkanes, *J. Org. Chem.*, Vol. 22, pages 837–838 (1957); Lasslo et al, Substituted Piperidinecarboxamides, *J. Org. Chem.*, Vol. 21, pages 958–960 (1956); Quintana et al, Synthesis of Selected Amines of Mono- and Bis(carboxypiperidino)alkanes, *J. Pharm. Sci.*, Vol. 52, pages 1186–1188 (1963); Beasley et al, The Effect of Piperidinecarboxamide Derivatives on Isolated Human Plasma Cholinesterase. II. Variations in the Amide Function, *J. Med. Chem.*, Vol. 7, pages 698–701 (1964); Quintana et al, Synthesis of Carbamoylpiperidine-type Cholinesterase Inhibitors, *J. Pharm. Sci.*, Vol. 54, pages 785–787 (1965); Quintana et al, Substituted 1-Benzyl-3-(N,N-diethylcarbamoyl)piperidine Cholinesterase Inhibitors. Relationships Between Molecular Constitution, $pK_a'$ Values, and Partition Coefficients, *J. Med. Chem.* Vol. 10, pages 1178–1180 (1967); and Quintana et al, Relationships Between the Chemical Constitution of Carbamoylpiperidines and Related Compounds, and Their Inhibition of ADP-Induced Human Blood Platelet Aggregation, *Thromb. Res.*, Vol. 22, pages 665–680 (1981).

The invention will be illustrated by the following non-limiting examples.

Adenosine diphosphate (ADP) was used to induce platelet aggregation and was utilized as the sodium salt. A 10 mM stock solution was prepared fresh before each use in modified Tyrode's buffer and working dilutions were prepared with modified Tyrode's buffer immediately prior to use. The buffer contained NaCl (137.00 mM), KCl (2.70 mM), NaHCO$_3$ (11.90 mM), NaH$_2$PO$_4$.H$_2$O (0.36 mM) and glucose (5.60 mM) in redistilled water. Adjustment to pH 7.4 was effected by addition of 1N HCl.

Venous blood for the examples set forth below was collected in plastic syringes from eight healthy male volunteers (aged 22–30 years) who had fasted overnight and had abstained from all medications, alcohol, tobacco and caffeine for a period of at least one week prior to donations. The blood was transferred into siliconized centrifuge tubes containing 3.2% sodium citrate (blood/citrate ratio 8:1) and centrifuged at 120×g for 15 minutes at 23° C., yielding platelet-rich plasma (PRP); platelet-poor plasma (PPP) was obtained by centrifugation of citrated whole blood at 1,100×g for 15 minutes at 23° C. The platelet count of PRP was determined and adjusted to a final count of 300,000 platelet per mm$^3$ by dilution with autologous PPP. (Occasionally, blood from a given donor yielded PRP with a count lower than the stipulated figure; however, this was usually greater than 285,000, and never less than 250,000 platelets per mm$^3$.) The plasma so obtained was transferred in 1.2-ml aliquots to siliconized glass tubes, by means of a siliconized Pasteur pipet. In order to maintain plasma pH in the appropriate range, the air in the tubes are displaced gently (1 minute) with a 5% (CO$_2$-95% air (v/v) mixture and the tubes sealed with Parafilm according to the method of Han et al, *Br. J. Haematol*, Vol. 26, pages 373–389 (1974). The plasma was maintained at 37° C. in a water bath until used in the aggregation experiments.

Assays of platelet aggregation were performed at least in duplicate, using plasma acquired from different donors, employing a method developed by Quintana et al (Quintana et al, Relationships Between the Chemical Constitution of Carbamoylpiperidines and Related Compounds, and Their Inhibition of ADP-Induced Human Blood Platelet Aggregation, *Thromb. Res.* Vol. 22, pages 665–680 (1981); Quintana et al, Effects of Ethanol and of Other Factors on ADP-Induced Aggregation of Human Blood Platelets in Vitro, *Thromb. Res.* Vol. 20, pages 405–415 (1980))(cf. Born, *Nature*, Vol. 194, pages 927–929 (1962) and Mustard et al, *J. Lab. Clin. Med.*, Vol. 64, pages 548–559 (1964)).

Initially, in each experiment, 0.45-ml aliquots of PRP were placed in siliconized cuvettes and stirred (1,100 rpm) in the aggregometer at 37° C. to ascertain the absence of spontaneous aggregation. Appropriate ADP solutions (50 μl) were subsequently injected using a Hamilton microliter syringe to determine the minimal concentration eliciting maximal biphasic aggregation. This ranged from 2 μM to 8 μM (average 4.7±1.1 μM) for 84 plasma samples (cf. Quintana et al, Effects of Ethanol and of Other Factors on ADP-Induced Aggregation of Human Blood Platelets in Vitro, *Thromb. Res.* Vol. 20, pages 405–415 (1980). In each case, the concentration of ADP so determined was used in eliciting aggregation throughout each specific set of aggregometric evaluations.

0.5 μl of a solution of the evaluant compound in redistilled 95% ethanol was injected into a stirred (1,100 rpm) 0.45-ml aliquot of plasma in a siliconized cuvette in the aggregometer-well (37° C.). After 15 seconds, the cuvette was transferred to an incubator (also at 37° C.) and the contents held at this temperature, without stirring, until 2 minutes post-injection. The cuvette was then returned to the aggregometer-well, a base-line being recorded for 2 minutes to detect any spontaneous aggregation. At exactly 4 minutes after injection of the evaluant solution, 50 μl of the appropriate ADP solution was injected and aggregation recorded for 5 minutes. Evaluants were studied at one or more of the following final concentrations: 100 μM, 50 μM, 10 μM and 5 μM. Control experiments (ethanol in a final concentration of 0.095% v/v) were performed in parallel with those involving the respective evaluants, and were initiated either 1 minute prior to or 1 minute after the start of experiments employing the test compounds. This permitted injections to be made precisely at the specified times. Normally, 2 pairs of aggregations were carried out (at 70/71 and 80/81 minutes post-venipuncture). Evaluant and control aggregations were studied in alternate ($Y_1$ or $Y_2$) channels of the dual-channel aggregometer in order to detect any effects due to malfunction of a specific channel.

The pH of a sample of the plasma employed in aggregometric studies was routinely measured at 37° C. after the ADP-injection at 70/71 minutes post-venipuncture. Also, the pH of a second plasma sample, maintained at 37° C. under 5% $CO_2$–95% air mixture, was determined at the conclusion of the 80/81 minute aggregation-pair (e.g., 88 minutes from venipuncture). The readings ranged from 7.48–7.69 in both instances. Plasma pH was not affected perceptibly by the addition of representative evaluants in concentrations employed in this investigation.

In evaluating aggregometric tracings, primary attention was paid to intensity of aggregation, i.e., the maximum change in percentage of light transmittance with special attention to any abolition or diminution of the secondary and even the primary aggregation-waves. (Roper et al, *Am. J. Clin. Pathol.*, Vol. 71, pages 263–268 (1979); Mills et al, *Life Sci.*, Vol. 14, pages 659–672 (1974); Newhouse and Clark, in Triplett (Ed.), *Platelet Function; Laboratory Evaluation and Clinical Application.* Chicago, American Society of Clinical Pathologists, 1978, pages 109–121). Inhibition of platelet aggregation was graded in conformance with the following criteria: 0, slight potentiation (10% or less) or inhibition not exceeding 10%; 1+, 11–19% inhibition; 2+, 20–29% inhibition; 3+, 30–39% inhibition; 4+, 40–49% inhibition; 5+, 50–59% inhibition; 6+, inhibition 60% or greater. The secondary aggregation wave was observed to be abolished by inhibitory responses rated 3+ or higher. Effects on the primary aggregation wave were normally evident only in inhibitions rated 4+ or higher.

Relationships between the molecular constitution of the evaluant-compounds and their inhibitory effects on platelet aggregation (Quintana et al, Relationships Between the Chemical Constitution of Carbamoylpiperidines and Related Compounds, and Their Inhibition of ADP-Induced Human Blood Platelet Aggregation, *Thromb. Res.*, Vol. 22, pages 665–680 (1981); Quintana et al, Interaction of Human Blood Platelet Aggregation Inhibitors with Phospholipid Films, *Thromb. Res.*, Vol. 24, pages 379–395 (1981); Quintana et al, Surface Activity and Human Blood Platelet Aggregation-Inhibitory Potency, *Chem-Biol.* Interactions, Vol. 38, pages 135–144 (1982); Quintana et al, Human Blood Platelet Aggregation Inhibitory Target Sites Assumed to Involve Membrane Phospholipids, *Biophys. J.*, Vol. 37, pages 130–133 (1982) are summarized in Table 1. Under conditions substantially comparable to those reported in *Thromb. Res.*, Vol. 22, pages 665–680 (1981), the compounds of the invention are capable of inhibiting thrombin-induced aggregation without eliminating thrombin-effected clotting. E.G., Compound 18 in Table 1 inhibits aggregation around 86%, but fails to abolish the characteristic clotting effect of thrombin.

TABLE 1

Relationships Between Chemical Constitution and Inhibition of Human Blood Platelet Aggregation 1. Mono- and Bis-substituted Alkanes $$CH_2-(CH_2)_n-CH_3$$
$$|$$
$$R$$

| R: | n: | No: | Inhibition |
|---|---|---|---|
| cyclohexyl-N.HBr | 8 | 1 | 2+ at 50 μM |
| cyclohexyl(CON($C_2H_5$)$_2$)-N.HBr *,† 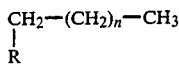 | 8 | 2 | 2+ at 50 μM |
| cyclohexyl(CON($C_2H_5$)$_2$)-N.HBr | 4 | 3 | 2+ at 100 μM |

TABLE 1-continued
Relationships Between Chemical Constitution and Inhibition of Human Blood Platelet Aggregation

| Structure | | No: | Inhibition |
|---|---|---|---|
| cyclohexyl-CON(C₂H₅)₂ with N.HBr | 0 | 4 | 0 at 100 μM |

$$CH_2-(CH_2)_n-CH_2$$
$$\ \ |\ \ \ \ \ \ \ \ \ \ \ \ \ \ \ \ \ \ |$$
$$\ \ R\ \ \ \ \ \ \ \ \ \ \ \ \ \ \ \ R$$

| R: | n: | No: | Inhibition |
|---|---|---|---|
| pyridinium N+Br⁻ | 8 | 5 | 0 at 100 μM |
| piperidine N.HBr | 8 | 6 | 4+ at 50 μM |
| 4-CON(C₂H₅)₂ piperidine N.HBr | 8 | 7 | 4+ at 50 μM |
| 3-CON(C₂H₅)₂ piperidine N.HBr ‡ | 8 | 8 | 5+ at 50 μM |
| 3-CON(C₂H₅)₂ piperidine N.HBr | 4 | 9 | 5+ at 50 μM |
| 3-CON(C₂H₅)₂ piperidine N.HCl | 1 | 10 | 2+ at 100 μM |
| 3-CON(C₂H₅)₂ piperidine N.HBr | 0 | 11 | 1+ at 100 μM |

*The corresponding completely unsaturated (pyridinium bromide) 12 (2+ at 100 μM) and partly unsaturated (Δ³,⁴-tetrahydro, hydrochloride) 13 (1+ at 100 μM) derivatives are much less active.
† The monoethyl, hydrobromide, 14 (3+ at 100 μM) and the unsubstituted, hydrobromide, 15 (2+ at 100 μM) congeners are also less potent.
‡ The dimethylamide, dihydrobromide, analog 16 is less effective (4+ at 100 μM).

2. Mono- and bis-substituted xylenes

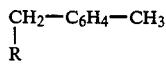

| R: | No: | Inhibition |
|---|---|---|

TABLE 1-continued
Relationships Between Chemical Constitution and Inhibition of Human Blood Platelet Aggregation

| Structure | No: | Inhibition |
|---|---|---|
| piperidine-CON(C₂H₅)₂, N.HBr | 17 | 1+ at 100 μM |

$$CH_2-C_6H_4-CH_2$$
with R substituents:

| R: | No: | Inhibition |
|---|---|---|
| piperidine-CON(C₂H₅)₂*, N.HBr | 18 | 2+ at 5 μM |
| pyridinium-CON(C₂H₅)₂*, N⁺Br⁻ | 19 | 0 at 100 μM |
| piperidine-CON(C₂H₅)₂⁺, N.HBr | 20 | 0 at 50 μM |
| piperidine-CON(C₂H₅)₂⁺⁺, N.HCl | 21 | 3+ at 50 μM |

*bis - para
⁺bis - ortho
⁺⁺bis - meta

3. bis-substituted alkenes and alkyne

| No: | | Inhibition |
|---|---|---|
| 22 | (C₂H₅)₂NOC—piperidine(N.HCl)—CH₂—CH=CH—CH₂—piperidine(N.HCl)—CON(C₂H₅)₂ | 4+ at 100 μM |
| 23 | (C₂H₅)₂NOC—piperidine(N.HCl)—CH₂—C≡C—CH₂—piperidine(N.HCl)—CON(C₂H₅)₂ | 0 at 100 μM |

TABLE 1-continued
Relationships Between Chemical Constitution and Inhibition of Human Blood Platelet Aggregation

| 24 | 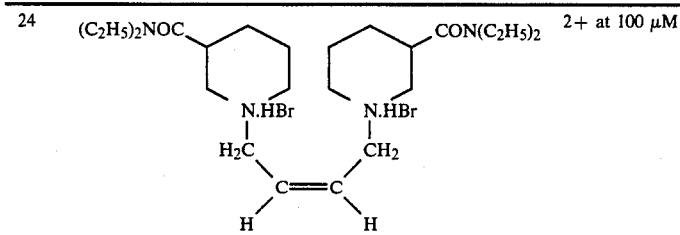 | 2+ at 100 μM |
|---|---|---|

Essentially, the bis-dialkylcarbamoylpiperidino-substituted decane 8 and hexane 9 analogs are equally active (5+ at 50 μM; Table 1). This indicates that the distance between the ring nitrogens separated by a hexamethylene link ($C_6$) matches closely that of the target sites on the platelet surface. The ring nitrogens on the decamethylene chain ($C_{10}$), through appropriate buckling of that flexible link, can also connect readily with the same target sites. However, since the ring nitrogens of the bis-dialkylcarbamoylpiperidino-substituted ethane 11 separated by only two methylene groups ($C_2$) could not accommodate a comparable reach, this analog is ten times weaker (1+ at 100 μM; Table 1).

On the other hand, the mono-substituted decane 2 (2+ at 50 μM) is twice as potent as the hexane 3 (2+ at 100 μM) (Table 1); the hydrophobic bonding of the former ($C_{10}$) on the platelet surface adjacent to the target site is so strong that it substantially augments the interaction of its single piperidino nitrogen with one target site. Conversely, in the mono-substituted hexane, the shorter alkyl chain ($C_6$) is unable to exert hydrophobic bonding of comparable magnitude. Not surprisingly, such hydrophobic forces are not discernible at all in the mono-substituted ethane 4 which does not register any activity at the same concentrations (0 at 100 μM, Table 1).

Overall, the bis-substituted derivatives are decidedly more potent than the mono-substituted ones (i.e., 6>1, 8>2, 9>3, 11>4, 18>17). Since this observation applies also to compounds lacking carbamoyl functions (6>1), the nitrogens in the piperidine rings obviously play a prominent role. The influence of the carbamoyl function, and of its location on the piperidine ring, is further reflected in the data generated by 7, 8 and 16. Notably, the aggregation-inhibitory potency of the mono- and bis-substituted alkanes follows that of their surface activity. Especially interesting is the parallel between increasing hydrophobic character and inhibition of aggregation even in the sub-series focusing on the amide function. 2>14>15, Table 1, refer also to second footnote: 2, 2+ at 50 μM, $PC_{rel.}$ 52.7; 14, 3+ and 100 μM, $PC_{rel.}$ 12.7; 15, 2+ at 100 μM, $PC_{rel.}$ 1.0 ($PC_{rel.}$ = benzene/water relative partition coefficients). The influence of introducing a double bond at $\Delta^{3,4}$, distorting the ring structure and enhancing the compound's polar character through the conjugation of the amide function, may well result in lesser hydrophobicity and thereby account for the lesser effect of 13 (1+ at 100 μM; (see first footnote in Table 1) compared to 2 (2+ at 50 μM).

The data of Table 1 unequivocally indicate that increasing lipophilic character contributes to potency, especially in the mono-substituted alkanes. The results also suggest that the bis-substituted derivatives could well interact with two target sites on the platelet surface whenever the polymethylene chain is long enough to accommodate such interaction. The latter contention is materially substantiated by the potency of the bis-dialkylcarbamoylpiperidino-para-xylene 18. It was decidedly active (2+) at 5 μM, completely abolished the secondary aggregation wave (4+) at 10 μM and almost eliminated the primary wave (6+) at 50 μM. This compound could be envisioned as a close but substantially more potent analog of the bis-substituted hexane 9, in which four of the six methylene units have been replaced by a phenylene moiety. While this should not affect perceptibly the hydrophobic character of the molecule, the planarity of the ring structure renders 18 much more rigid than 9.

Moreover, the intramolecular distances between the ring nitrogens, computed with Godfrey space-filling models, register for the former a range of 7.8–8.3 Å with a flexibility variance of 0.5 Å, and for the latter a range of 4.4–9.1 Å with a flexibility variance of 5.7 Å. Compound 9, in which the range of ring nitrogen distances encompasses those of 18, is less active due to the almost ten-fold increase in the flexibility variance. And, remarkably, while the bis-substituted xylylene 18 registered a 2+ activity at 5 μM concentration, its mono-substituted analog 17 was only half as active (1+) at twenty times higher concentrations (100 μM). The significance of the interatomic distance between the ring nitrogens in the bis-substituted compounds is further corroborated by the decreasing activities of the correspondingly substituted meta-xylene 21 (5.3–7.8 Å) and ortho-xylene 20 (4.8–5.9 Å) analogs. These data distinctly suggest platelet membrane target sites spaced at about 8 Å.

Despite the striking potency of 18 (2+ at 5 μM), its bis(dialkylcarbamoylpyridinium) congener 19 was completely inactive at twenty times higher concentrations (0 at 100 μM). This paralleled the findings for 6>5 and 2>12. While, in the mono-substituted series, the 3-(N,N-diethylcarbamoyl)pyridinium analog 12 did register activity (2+ at 100 μM), this could be accounted for by the additional hydrophobicity contributed through the two ethyl substituents on the carbamoyl function. The behavior of 19, 12 and 5 could be attributed (i) to the aromatic character of the ring structure and its conjugation with the amide function, or (ii) to the charge level of the ring nitrogen, or (iii) to both. Each factor individually, or both in combination, could lessen hydrophobicity and reduce aggregation inhibitory potency. As quaternary amines, the heterocyclic nitrogens retain the same charge regardless of their environment and consequently, in a biosystem, their hydrophobicity does not even approximate that of corresponding tertiary amines which are generally subject to broad variances in protonation contingent upon the pH of the medium and the specific compounds' $pK_a$ values. This very trait of tertiary amines provides appropriate hydrophobic character for their penetration of the platelet membrane's lipid bilayer without interfering with the subsequent generation of adequate cationic species.

The impact of stereoisomerism lends itself also, in part, to interpretation in terms of intramolecular distances of pivotal functions. The greater potency of the trans-isomer 22 compared to the cis-analog 24 can be attributed readily to the fact that the intramolecular distance of its ring nitrogens (5.9–6.3 Å) is closer to the postulated optimum of 8 Å than the somewhat, but decidedly, lesser one computed for the rings' heteroatoms in the cis-compound (5.4–6.1 Å). It should be noted that the increased polarity effected by unsaturation in the alkyl chain contributes considerably to their comparatively low level of activity. Accordingly, it should not be surprising that 23 registers no activity at 100 μM concentration. The hydrophobic fragmental constant for its alkyl chain of four carbons with one triple bond is 1.371 compared to that of 1.791 for the corresponding linkage in 22 and 24 with one double bond segment, and to that of 2.108 for a corresponding alkyl chain without any unsaturation. It is obvious that 23 is the most polar compound among those depicted.

It would appear that the carbamoylpiperidines and related compounds are highly effective by penetrating the lipid bilayer of the platelet membrane and by interacting as cations with negatively charged phospholipids (e.g., phosphatidylserine and phosphatidylinositol within the bilayer's inner segment. It would further appear that, in the event of such penetration, the cationic forms of the compounds interfere with phospholipase activation by counteracting stimulus-induced mobilization of $Ca++$ ions and $Ca++$-dependent phospholipase activity. It would also appear that activity is dependent upon (i) intramolecular distances between and charge levels of pivotal atoms and/or functions, (ii) molecular geometry and flexibility, and (iii) hydrophobic characteristics of molecular segments.

The interaction of carbamoylpiperidine and related entities with the lipid bilayer of platelet plasma membranes can be demonstrated by the behavior of the compounds in monomolecular film systems employing prototype phospholipids matching the salient structural features of actual platelet plasma membrane constituents (Quintana et al, Interaction of Human Blood Platelet Aggregation Inhibitors with Phospholipid Films, *Thromb. Res.*, Vol. 24, pages 379–395 (1981). The investigation included experiments at 34.0 mN $m^{-1}$, the surface pressure estimated to occur in the actual platelet plasma membrane, and at pH values approximating those employed in the hemodynamic study. Phosphatidylserine (PS) and phosphatidylinositol (PI) are reported to be almost entirely confined to the inner segment of the bilayer; phosphatidylethanolamine (PE) is also believed to be primarily a constituent of the bilayer's inner leaflet; and phosphatidylcholine (PC) is known to be located within the bilayer's outer leaflet in material quantities. The compounds with potent platelet aggregation inhibitory effects show correspondingly strong levels of "specific" interaction with some of the phospholipids and very little intercourse, if any, with others. Their very limited interaction with PE is especially revealing.

The following compounds were tested. The numbers refer to their listing in Table 1. All of the compounds were analytically pure. They include: 1,4-alkylenebis[3-(N,N-diethylcarbamoyl)piperidine hydrobromide] (compound 18); 1,4-xylylenebis[3-(N,N-diethylcarbamoyl)pyridinium bromide] (compound 19); 1-(p-methylbenzyl)-3-(N,N-diethylcarbamoyl)piperidine hydrobromide (compound 17 ); 1,10-bis[3-(N,N-diethylcarbamoyl)piperidino]decane dihydrobromide (compound 8); 1-decyl-3-(N,N-diethylcarbamoyl)piperidine hydrobromide (compound 2); 1,2-bis[3-(N,N-diethylcarbamoyl)piperidino]ethane dihydrobromide (compound 11); 1-ethyl-3-(N,N-diethylcarbamoyl)piperidine hydrobromide (compound 4).

The phospholipids utilized were: phsophatidylserine (bovine; fatty acid comp. $C_{16:0}$ 3%; $C_{18:0}$ 42%, $C_{18:1}$ 37%, $C_{18:2}$ 2%, others 16%), phosphatidylinositol (plant; fatty acid comp. $C_{16:0}$ 48%, $C_{18:1}$ 5%, $C_{18:2}$ 43%, $C_{18:3}$ 4%) and phosphatidylethanolamine (bovine; fatty acid comp. $C_{16:0}$ 10%, $C_{18:0}$ 20%, $C_{18:1}$ 58%, $C_{20:0}$ 12%); they had formula weights of 788, 901 and 744, respectively, based on the dioleoyl form. Phosphatidylcholine was synthetic dioleoyl-L-α-lecithin, formula weight 804.1. All phospholipids were pure and homogeneous as determined by one- and two-dimensional thin-layer chromatography. The properties of the stearic acid employed have been described (Quintana et al, *J. Pharm. Sci.*, Vol. 56, pages 1193–1194 (1967)).

Surface-pressure and surface-potential measurements were carried out concurrently with the following instrumentation. It consisted of an environment-controlled chamber (dimensions: 15"×21"×18") housing a Teflon trough (25 cm×10.1 cm×2 cm) and incorporating (i) an automatic compression-barrier drive, (ii) means for remote stirring of the subphase, (iii) temperature and atmosphere control and, (iv) copper wire electrical shielding. Surface pressures were determined with a Wilhelmy-type surface balance; a sand-blasted, 5 cm perimeter platinum plate was connected to a universal transducing cell with UL5 micro-scale accessory and SC1001 universal transducer readout. Surface potentials were determined by the ionizing electrode method [Gaines, Insoluble Monolayers at Liquid-Gas Interfaces, N.Y. Wiley Interscience, 1966, pages 44–50 and 73–79] employing an electrometer, an air electrode and a platinum trough electrode. The output of the surface pressure and potential measurements was fed to a dual pen recorder. A continuous gentle flow of moist nitrogen was circulated through the chamber by means of a gas dispersion tube positioned over the center of the trough to minimize (i) oxidation of phospholipids in the film, (ii) evaporation of subphase water, and (iii) changes in the surface concentration of monolayers. The temperature of the subphase in the trough and that of the chamber's environment were monitored with probes. The subphase temperature was maintained at 25.0±0.2° C. by circulating water from a circulator through a built-in compartment jacketing the entire trough, and the chamber's environmental temperature normally ranged 24° to 26° C.

Subphase water was obtained by redistillation from aqueous potassium permanganate through a 45-cm Vigreaux column. Its surface tension averaged 72.1±0.9 mN $m^{-1}$ (mean±mean deviation for 75 experiments) and its pH was 6.08±0.10. Hydrogen ion concentration was determined with an expanded-scale research pH meter. Phosphate buffer (pH 7.60) consisted of reagent-grade $Na_2HPO_4$ (0.05756M) and $NaH_2PO_4.H_2O$ (0.009137M) in redistilled water. Its surface tension was 72.5±0.7 mN m$^{-1}$ (14 experiments).

Redistilled water (or buffer) (550 ml) was placed in the trough of the surface balance and the surface was cleaned twice with Teflon sweeping bars. A stationary barrier (Teflon weighted with brass) was positioned at one end of the trough and the compression barrier of the same construction 20.5 cm from the latter. Subsequently, the surface tension ($\gamma_o$) and potential ($V_o$) of the subphase were recorded during a 90-min. period. A chloroform solution of the film-forming lipid was then deposited on the subphase with an Agla micrometer-syringe.

A computed total of 3.82×10$^{16}$ film molecules was generated normally by 0.0100 ml of a 6.34×10$^{-3}$M solution of PS. A computed total of 2.62×10$^{16}$ film molecules was generated normally (i) by 0.0079 ml of a 5.50×10$^{-3}$M solution of PI, (ii) by 0.0065 ml of a 6.72×10$^{-3}$M solution of PE, and (iii) by 0.0070 ml of a 6.22×10$^{-3}$M solution of PC. A computed total of 5.01×10$^{16}$ film molecules was generated normally by 0.0200 ml of a 4.16×10$^{-3}$M solution of stearic acid. Calculating evaluant/phospholipid ratios for our compounds at 1×10$^{-4}$M concentration, yielded: 874 evaluant molecules per molecule of PS, 1270 evaluant molecules per molecule of PI, or PE, or PC, and 667 evaluant molecules per molecule of stearic acid. At 1×10$^{-5}$M and at 1×10$^{-6}$M concentrations the number of evaluants per phospholipid decreased to 87/1, 127/1, 67/1 and 8.7/1, 12.7/1, 6.7/1, respectively.

After a 15-min. period (to allow the solvent to evaporate) the film was compressed by advancing the compression barrier at a rate of 0.25 cm min$^{-1}$ to the desired initial surface pressure ($\pi_i$=8.5, 17.0, or 34.0 mN m$^{-1}$; $\pi_i$—$\gamma_f$, $\pi_i$ being the change in surface tension effected by the film, $\gamma_o$ the surface tension value of the subphase per se, and $\gamma_f$ the surface tension of the film-covered subphase. The surface pressure was, then, maintained at $\pi_i$, and the potential was allowed to equilibrate, for 90 min. ($\pi_i$, after being maintained at that pressure for 90 min., becomes ($\pi_f$)$_{90}$; and $\Delta V_{90}$=($V_f$)$_{90}$−($V_o$)$_{90}$). Employing a glass syringe fitted with a glass needle, 5.0 ml of a solution of the evaluant-compound in redistilled water (or buffer) was then injected into the subphase behind the compression barrier. The desired final subphase concentration (1×10$^{-4}$M, 1×10$^{-5}$M or 1×10$^{-6}$M) of the evaluant was obtained by gently moving, through remote means, a Teflon-coated stirring bar, immersed in the subsolution over the length of the trough; normally, 25 cycles were employed over a period of 15-20 min. Changes in surface pressure ($\Delta\pi$) and in surface potential [$\Delta(\Delta V)$] were then monitored over an additional 90-min. period; values representing equilibrated interaction at 90 min. were recorded as $\Delta\pi_{90}$ and $\Delta(\Delta V)_{90}$, respectively. $\Delta\pi_{90}$=($\pi_{f+e}$)$_{90}$−($\pi_f$)$_{90}$; where ($\pi_{f+e}$)$_{90}$ is the surface pressure resulting from the interaction between the film and evaluant after 90-min. equilibration, and ($\pi_f$)$_{90}$ is $\pi_i$ maintained at that pressure for 90 min. $\Delta(\Delta V)_{90}$=($\Delta V_{f+e}$)$_{90}$−($\Delta V_f$)$_{90}$; where ($\Delta V_{f+}$)$_{90}$ is the surface potential resulting from interaction between the film and evaluant after 90-min. equilibration and ($\Delta V_f$)$_{90}$ is the surface potential of the film-subphase system at ($\pi_f$)$_{90}$.

Corresponding experiments were conducted in which solutions of the evaluant compounds were injected into subphases in the absence of a film, and surface pressures ($\pi_{90}$) and surface potentials ($\Delta V_{90}$) evident at 90 min. after cessation of stirring were recorded. In addition to serving as base line and control runs, the data so generated reflected the compounds' "nonspecific" surface activity within the context of the evaluations. At least two independent determinations of each, in the presence and the absence of films, were used to compute average values for the effect of each evaluant on surface pressure and potential. The individual determinations usually did not differ from computed mean values for surface pressure by more than 1.0 mN m$^{-1}$; in most instances they were below 0.5 mN m$^{-1}$ and did not exceed 1.9 mN m$^{-1}$. Normally, surface potential measurements did not deviate from computed mean values by more than 10 mV. In most instances they were below 5 mV and did not exceed 18 mV.

The results are set forth in Tables 2-6.

TABLE 2

Interaction of 1,4-Xylylenebis [3-(N,N—diethylcarbamoyl)piperidine Hydrobromide] (18) in 1 × 10$^{-4}$ M Concentrations with Monolayer Films on Water Subphase*

| Surface Pressure, mN m$^{-1}$ | | | Surface Potential, mV | |
|---|---|---|---|---|
| $\pi_i$ | $\Delta\pi_{90}$ | Film | $\Delta(\Delta V)_{90}$ | $\Delta V_{90}$ |
| 34.0 | +7.3 ± 0.1 | Phosphatidyl-serine | +104 ± 14 | +317 ± 2 |
| 17.0 | +18.2 ± 0.4 | | +193 ± 18 | +235 ± 5 |
| 8.5 | +18.8 ± 0.8 | | +199 + 11 | +217 ± 2 |
| 17.0 | +18.1 ± 0.4 | Phosphatidyl-inositol | +280 ± 7 | +202 ± 17 |
| 17.0 | +1.5 ± 0.2 | Phosphatidyl-ethanolamine | +98 ± 5 | +230 ± 0 |
| 34.0 | −0.7 ± 0.0 | Phosphatidyl-choline | +39 ± 12 | +439 ± 5 |
| 17.0 | −0.1 ± 0.0 | | +50 ± 6 | +363 ± 6 |
| 8.5 | +0.9 ± 0.2 | | +64 ± 3 | +318 ± 5 |
| 17.0 | −0.3 ± 0.6 | Stearic Acid | +65 ± 4 | +314 ± 2 |

*In the absence of a monolayer, Compound 18 generated $\pi_{90}$ = +0.3 ± 0.3 mN m$^{-1}$, $\Delta V_{90}$ = +119 ± 2 mV.

TABLE 3

Interaction of 1,4-Xylylenebis[3-N,N—diethylcarbamoyl)piperidine Hydrobromide] 18 in 1 × 10$^{-4}$ M Concentrations with Monolayer Films on Phosphate Buffer (pH 7.60) Subphase*

| Surface Pressure, mN m$^{-1}$ | | | Surface Potential, mV | |
|---|---|---|---|---|
| $\pi_i$ | $\Delta\pi_{90}$ | Film | $\Delta(\Delta V)_{90}$ | $\Delta V_{90}$ |
| 17.0 | +8.1 ± 0.4 | Phosphatidyl-serine | +95 ± 8 | +237 ± 12 |
| 17.0 | +8.1 ± 0.5 | Phosphatidyl-inositol | +132 ± 3 | +166 ± 11 |
| 17.0 | +3.0 ± 0.2 | Phosphatidyl-ethanolamine | +37 ± 2 | +250 ± 6 |
| 17.0 | +1.2 ± 0.0 | Phosphatidyl-choline | +19 ± 5 | +349 ± 16 |

*In the absence of a monolayer, Compound 18 generated $\pi_{90}$ = +5.9 ± 0.2 mN m$^{-1}$, $\Delta V_{90}$ = +367 ± 15 mV.

TABLE 4

Interaction of 1-(p-Methylbenzyl)-3-(N,N—diethylcarbamoyl)piperidine Hydrobromide] 17 in 1 × 10$^{-4}$ M Concentrations with Phosphatidylserine Monolayer Films at $\pi_i = 17.0$ mN m$^{-1}$

| Surface Pressure, mN m$^{-1}$ | | | | Surface Potential, mV | | |
|---|---|---|---|---|---|---|
| Subphase Only $\pi_{90}$ | Film and Subphase $\Delta\pi_{90}$ | Subphase | % In Ionized Form | Film and Subphase $\Delta(\Delta V)_{90}$ | $\Delta V_{90}$ | Subphase Only $\Delta V_{90}$ |
| +0.4 ± 0.2 | +12.1 ± 0.5 | Water (pH 6.07)* | 98.6 | +105 ± 17 | +258 ± 8 | +98 ± 18 |
| +1.0 ± 0.2 | +5.0 ± 0.6 | Phosphate Buffer (pH 7.60)* | 67.1 | +69 ± 3 | +248 ± 14 | +140 ± 3 |

*Mean of 4 experiments

TABLE 5

Relationship Between Structural Characteristics of Carbamoylpiperidino- and -pyridinium-aralkanes, Their Human Blood Platelet Aggregation Inhibitory Potency and Their Interaction in 1 × 10$^{-4}$ M Concentrations With Phosphatidylserine Monolayer Films on Water Subphase at $\pi_i = 17.0$ mN m$^{-1}$.

| Surface Pressure, mN m$^{-1}$ | | | | Surface Potential, mV | |
|---|---|---|---|---|---|
| Subphase Only $\pi_{90}$ | Film and Subphase $\Delta\pi_{90}$ | Compd. No. | Platelet Aggregation Inhibitory Potency | Film and Subphase $\Delta(\Delta V)_{90}$ | Subphase Only $\Delta V_{90}$ |
| +0.3 ± 0.4 | +4.8 ± 1.2 | 19 | 0 at 1 × 10$^{-4}$ M | +82 ± 5 | +51 ± 4 |
| +0.3 ± 0.3 | +18.2 ± 0.4 | 18 | 2+ at 5 × 10$^{-6}$ M | +193 ± 18 | +119 ± 2 |
| +0.4 ± 0.2 | +12.1 ± 0.5 | 17 | 1+ at 1 × 10$^{-4}$ M | +105 ± 17 | +98 ± 18 |

TABLE 6

Relationship Between Structural Characteristics of Carbamoylpiperidinoalkanes, Their Human Blood Platelet Aggregation Inhibitory Potency and Their Interaction in 1 × 10$^{-4}$ M Concentrations with Phosphatidylserine Monolayer Films on Water Subphase at $\pi_i = 17.0$ mN m$^{-1}$.

| Surface Pressure, mN m$^{-1}$ | | | | Surface Potential, mV | |
|---|---|---|---|---|---|
| Subphase Only $\pi_{90}$ | Film and Subphase $\Delta\pi_{90}$ | Compd. No. | Platelet Aggregation Inhibitory Potency | Film and Subphase $\Delta(\Delta V)_{90}$ | Subphase Only $\Delta V_{90}$ |
| +3.1 ± 0.4 | +20.0 ± 1.9 | 2 | 2+ at 5 × 10$^{-5}$ M | +199 ± 1 | +243 ± 12 |
| −0.4 ± 0.8 | +15.0 ± 1.3 | 8 | 5+ at 5 × 10$^{-5}$ M | +159 ± 2 | +154 ± 9 |
| +0.6 ± 0.2 | +8.4 ± 0.1 | 11 | 1+ at 1 × 10$^{-4}$ M | +133 ± 10 | +174 ± 7 |
| 0.0 ± 0.0 | −0.3 ± 0.6 | 4 | 0 at 1 × 10$^{-4}$ M | +42 ± 12 | +60 ± 5 |

Monolayer studies on the interaction of phospholipases with phospholipid films yielded estimates very close to 34.0 mN m$^{-1}$ for surface pressures in the platelet membrane. While the interaction of Compound 18 with PS on water was certainly significant at such initial surface pressures, it substantially increased at 17.0 mN m$^{-1}$, and remained the same at 8.5 mN m$^{-1}$ (Table 2). At $\pi_i$ 17.0 mN m$^{-1}$, in 1×10$^{-4}$M concentrations, Compound 18 interacted strongly with PI ($\Delta\pi_{90}$+18.1±0.4 mN m$^{-1}$) and PS ($\Delta\pi_{90}$+18.2±0.4 mN m$^{-1}$), barely with PE ($\Delta\pi_{90}$+1.5±0.2 mN m$^{-1}$) and not at all with PC ($\Delta\pi_{90}$−0.1±0.0 mN m$^{-1}$) (Table 2). The compound's effect on surface pressure and potential in PI and PS monolayer systems was, in fact, so strong that it continued to exert 87.3% ($\Delta\pi_{90}$+15.8±0.2 mN m$^{-1}$) and 91.2% ($\Delta\pi_{90}$+16.6±0.2 mN m$^{-1}$) at ten-fold lower concentrations, and retained 57.5% ($\Delta\pi_{90}$+10.4±0.3 mN m$^{-1}$) and 37.9% ($\Delta\pi_{90}$+6.9±0.9 mN m$^{-1}$) of its potency at one-hundred-fold dilution. Compound 8 (see Table 6) registered the same strength ($\Delta\pi_{90}$+15.0±1.3 mN m$^{-1}$) at 1×10$^{-4}$M and ($\Delta\pi_{90}$+15.6±1.3 mN m$^{-1}$) at 1×10$^{-5}$M concentrations, and retained 70.0% of its impact ($\Delta\pi_{90}$+10.5±0.5 mN m$^{-1}$) at 1×10$^{-6}$M concentration in PS monolayer systems. Compound 2, (see Table 6), displayed commensurate effects on PS films ($\Delta\pi_{90}$+20.0±1.9 mN m$^{-1}$ at 1×10$^{-4}$M; $\Delta\pi_{90}$+20.6±0.4 mN m$^{-1}$ at 1×10$^{-5}$M; $\Delta\pi_{90}$+12.7±0.5 mN m$^{-1}$ at 1×10$^{-6}$M). Corresponding trends were observed for the surface potential values [$\Delta(\Delta V)_{90}$]; viewing them as an indicator, the respective levels of interaction PI>PS>PE>PC are in accord with the ionic characters of these phospholipids.

A similar, although less striking, trend (PI>PS>PE>PC) is evident in experiments conducted with phospholipid films spread on a phosphate buffer (pH 7.6) subphase (Table 3). As noted above, tertiary amines, like those in the molecular structure of the compounds herein, are generally subject to broad variances in protonation, contingent upon the pH of the medium and the specific compound's pK$_a$ value. Therefore, changing from a water (pH 6.08 and a higher proportion of cationic species) to a phosphate buffer (pH 7.60 and a lower proportion of cationic species) subphase substantially affected the extent of the compound's interaction with PI and PS. This very trait of tertiary amines provides appropriate hydrophobic character for the penetration of the platelet membrane's lipid bilayer without interfering with the subsequent generation of adequate cationic species.

Compound 17, whose pK$_a$ (7.91) has been experimentally determined [Quintana et al, Substituted 1-Benzyl-3-(N,N-diethylcarbamoyl)piperidine Cholinesterase Inhibitors—Relationships Between Molecular Constitution, pK$_a$' Values, and Partition Coefficients, J. Med. Chem. 10, pp. 1178–1180, 1967] provides further documentation to this effect (Table 4). While at pH 7.60 it is 67.1% ionized and decidedly interacts with PS, that interaction for $\Delta\pi_{90}$ is 2.42 times stronger at pH 6.07 when it is 98.6% ionized. It should be noted that the compound is 87.1% ionized at pH 7.08, the mean intracellular value for platelets [at an extracellular pH of 7.4, the value registered for whole blood.] Along the same lines, but from a different slant, Compound 18 elicited considerable non-specific surface activity ($\pi_{90} = +5.9 \pm 0.2$ mN m$^{-1}$) in a filmless phosphate buffer subphase. It did not register any in a corresponding water subphase ($\pi_{90} = +0.3 \pm 0.3$ mN m$^{-1}$) (footnotes in Tables 2 and 3). While the former value remains below the ones observed with the PI and PS films even at pH 7.60, such non-specific surface activity could be decidedly lower at pH 7.08 in light of the previous considerations.

Two basic premises can be formulated based on the foregoing data: (i) Lower pH values will increase ionization of the evaluant and thereby, in the presence of a PS or PI film, will enhance cation-activated interaction with these phospholipids. (ii) Higher pH values will decrease ionization of the evaluant and thereby, in the absence of phospholipid films, will enhance its lipophilic characteristics which may or may not be sufficient to increase surface pressure.

The data strongly corroborate that the compounds possess appropriate hydrophobic character to penetrate the lipid bilayer of the platelet plasma membrane and, subsequently, are capable of generating sufficient quantities of their cationic species to counteract massively stimulus-induced mobilization of Ca++ ions and, thereby, restrain or void Ca++-dependent phospholipase activity. By means of this mechanism the compounds function as effective membrane stabilizing agents. There is corroborating evidence in the literature in support of these contentions. Vanderhoek and Feinstein [Vanderhoek et al, Local Anesthetics, Chlorpromazine and Propanolol Inhibit Stimulus-activation of Phospholipase-A$_2$ in Human Platelets, Mol. Pharmacol. 16, pp. 171–180, 1979] present especially convincing data and cite those of others [Sun et al, Enzymic Regulation of Arachidonate Metabolism in Brain Membrane Phosphoglycerides, Lipids 14, pp. 229–235, 1979; Rittenhouse-Simmons, Production of Diglyceride from Phosphatidylinositol in Activated Human Platelets, J. Clin. Invest. 63, pp. 580–587, 1979] in emphasizing the prominent function of Ca++ in controlling phospholipase-A$_2$ and phospholipase-C activity (Billah et al, Phospholipase A$_2$ and Phospholipase C Activities of Platelets, Differential Substrate Specificity, Ca$^{2+}$ Requirement, pH Dependence, and Cellular Localization, J. Biol. Chem. 255, pp. 10227–10231, 1980). The importance of hydrophobic character, in imparting appropriate affinity for molecules to consummate interaction leading to the prevention of Ca++ mobilization, was stressed by Lullmann et al [Ca Replacement by Cationic Amphiphilic Drugs From Lipid Monolayers, Biochem. Pharmacol. 20, 2969–2974, 1980]. While some of the literature tends to categorize, in several respects, PE with PI and PS [Chap et al, Organization and Role of Platelet Membrane Phospholipids as Studied with Purified Phospholipases, Agents Actions 9, pp. 400–406, 1979; Broekman et al, Phospholipid Metabolism in Stimulated Human Platelets. Changes in Phosphatidylinositol, Phosphatidic Acid and Lysophospholipids, J. Clin. Invest. 66, pp. 275–283, 1980; and Schick et al, Location of Phosphatidylethanolamine and Phosphatidylserine in the Human Platelet Plasma Membrane, J. Clin. Invest. 57, pp. 1221–1226, 1976], Compound 18 barely interacted with the former while registering massive interactions with the latter two. It appears that PE may not have a pivotal function in the aggregation inhibitory effect elicited by the compound. Interestingly, Dachery-Prigent and co-workers [Dachery-Prigent et al, Propranolol, Chlorpromazine and Platelet Membrane; A Fluorescence Study of the Drug—Membrane Interaction, Thromb. Res. 14, pp. 15–22, 1979] have also pointed out, within a different context, the potent reactivity of PS and PI compared to a complete lack of it in the case of PE.

The behavior of all of the compounds (i) in platelet aggregation studies, and (ii) in phospholipid monolayer systems appears to reflect, basically, the same reaction mechanisms. In correlating platelet aggregation inhibitory potency with the compounds' impact on PS monolayers, it is evident that they readily parallel each other (Tables 5 and 6); e.g., 18 > 8 > 17 and 11 > 19 and 4. In each instance, the compound with more hydrophobic character elicited greater changes in surface pressure and potential and increased platelet aggregation inhibitory strength; e.g., 18 > 19, 8 > 11, and 2 > 4.

In terms of monolayer studies, compounds 18, 19, 17, 8, 11 and 4 could be considered to exert "specific" action, since none registered significant effects on subphase surface tension in the absence of films ($\pi_{90} - 0.4 \pm 0.8$ mN m$^{-1}$ to $+0.6 \pm 0.2$ mN m$^{-1}$). Compound 2, on the other hand, elicited a $\pi_{90}$ value of $+3.1 \pm 0.4$ mN m$^{-1}$ which is by no means substantial but significant enough to signal that this compound's intercourse with PS ($\Delta\pi_{90}$) incorporates both "specific" and "non-specific" vectors. It should be noted that the referenced value was obtained at pH 5.78 and that the divergence between the $\pi_{90}$ values of this and the other analogs would be substantially amplified at pH 7.6. This, then, explains the compound's comparatively lesser platelet aggregation inhibitory potency; due to its "non-specific" activity, some of the compound dispensed into the aggregometric biosystem could well have been subject to sorption-loss on non-target sites and non-platelet proteins in the platelet-rich plasma which, in turn, could well have reduced the actual molecules available for interaction with platelet aggregation-inhibitory specific target sites.

The effects of Compound 19 on surface pressure and potential were not impressive, but significant; it had no activity at all, however, in inhibiting platelet aggregation. As stated previously, quaternary amines, like those in this compound, retain the same charges regardless of their environment which precludes their penetration of the platelet plasma membrane's lipid bilayer to its inner leaflet.

The compounds described hereinabove useful for the inhibition of blood platelet aggregation could be administered orally, parenterally, or rectally.

Employing computed plasma concentrations for aspirin, dipyridamole and sulfinpyrazone, the most frequently used antithrombotic agents in contemporary practice, it has been calculated that the most potent of the compounds of the invention are effective at lower levels. Although variances (i) in the extent and rate of absorption, (ii) in biodistribution and protein binding, and (iii) in the rate and diversity of biotransformation, compared to aspirin which induces 24% inhibition at 50

μM concentration (cf. Quintana et al, *Thromb. Res.*, 20: pp. 405-415, 1980), must be kept in mind, the most potent compounds of this invention effect 66% inhibition of ADP-induced blood platelet aggregation at 50 μM concentration, 46% at 10 μM, and 22% at 5 μM (Compound 18); or 53% at 50 μM (Compounds 8,9); or 51% at 50 μM (Compound 6); or 45% at 50 μM (Compound 7). The literature suggests an even lesser potency than aspirin for dipyridamole (10% at 250 μM concentration; Cucuianu et al, *J. Lab. Clin. Med.*, 77: pp. 958-974, 1971) and sulfinpyrazone (0% at 2,470 μM concentration; Packham et al., *J. Exp. Med.*, 126: pp. 171-188, 1967), even though it should be acknowledged that the latter two drugs could also act through alternate mechanisms.

The structure of the compounds of this invention would suggest a lower toxicity than those currently in use. Even aspirin's adverse effects are severe enough to counsel against its use by survivors of myocardial infarction (NHLBI-AMISRG, *J. Am. Med. Assoc.*, 243: pp. 661-669, 1980). Indeed, the compounds of this invention would appear to yield less toxic metabolites in the process of their biotransformation. In that respect, piperidine is known to be a natural metabolite and comparatively high quantities have been reported to occur in man (excretion in urine about 3 to 20 mg/day) (Williams, *Detoxication Mechanisms*, 2nd Edition, New York, John Wiley and Sons, 1959, p. 567). Piperidine-3-carboxylic acid (nipecotic acid) has not been discerned to have deleterious effects (Johnston, *Ann. Rev. Pharmacol. Toxicol.*, 18: pp. 269-289, 1978; cf. Krogsgaard-Larsen and Johnston, *J. Neurochem.*, 25: 797-802, 1975). Nicotinic acid (niacin) its aromatic analog, along with nicotinic acid amide (niacinamide), are known metabolites. Aminoalkanes or aralkanes which could be generated from some compounds of the invention are generally not known to be converted into harmful products (Williams, *Detoxication Mechanisms*, 2nd Edition, New York, John Wiley and Sons, 1959, pp. 128-130 and 146-147).

In broader terms of preventive medicine, it may be preferable to inhibit the adhesion-release-aggregation chain reaction at its very inception with platelet membrane stabilizing agents by precluding activation of phospholipases. This is especially true if it be considered that platelet cyclo-oxygenase inhibitors like aspirin incapacitate the patient's platelets for the rest of their life span (Walder et al, *Mol. Pharmacol.*, 13: pp. 407-414, 1977) and could possibly result in the concurrent inhibition of endothelial cyclo-oxygenase which would reduce or block generation of the endogenous aggregation inhibitor prostacyclin (PGI$_2$) (Moncada et al., in Gilman et al. (Eds.), *The Pharmacological Basis of Therapeutics*, 6th Edition, New York, MacMillan, 1980, p. 669; cf. Harris et al., *Ann. Rev. Physiol.*, 41: pp. 653-668, 1979).

Within the context of these considerations, the compounds of the invention could be formulated with suitable pharmaceutically acceptable carriers into a unit dosage form containing from about 28 to about 286 milligrams of active ingredient. Accordingly, orally administered dosages in the range of from about 0.38 to about 3.8 mg/kg of body weight per adult aminal, every six hours, would be sufficient to inhibit blood platelet aggregation; for infant or young animals, dosages in the range of from about 0.08 to about 0.76 mg/kg would be sufficient. Obviously, parenteral administration should reduce the referenced quantities, and rectal administration could also require a modification in the dosage.

We claim:

1. A method for the inhibition of blood platelet aggregation comprising administering to an animal in need thereof a blood platelet aggregation inhibiting amount of a compound selected from the group consisting of:

[A] A compound having the structural formula:

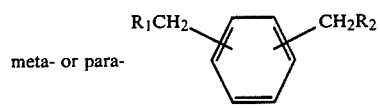

meta- or para-wherein
R$_1$ is

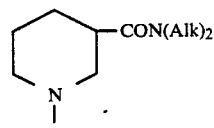

R$_2$ is H or

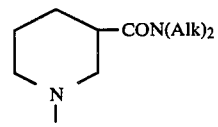

and
Alk is lower alkyl;

[B] A compound having the structural formula:

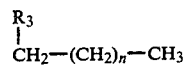

wherein
when R$_3$ is

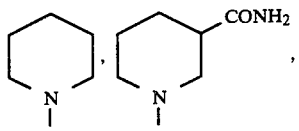

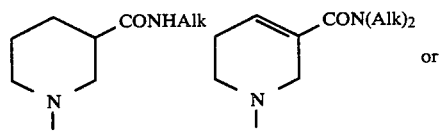

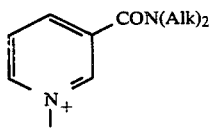

n is 8,
and
when R$_3$ is

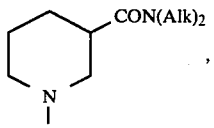

n is 4 or 8, and
Alk is lower alkyl;

[C] A compound having the structural formula:

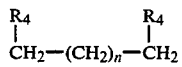

wherein
when $R_4$ is

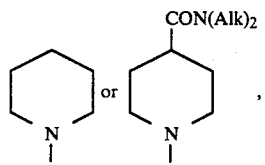

n is 8,
and
when $R_4$ is

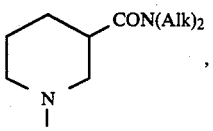

n is 0, 1, 4 or 8, and
Alk is lower alkyl;

[D] A compound having the structural formula:

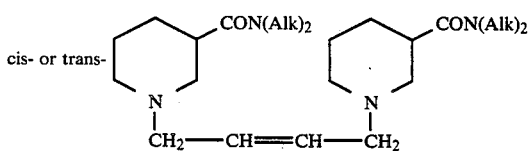

wherein
Alk is lower alkyl; and

[E] Addition salts thereof with pharmaceutically acceptable acids.

2. The method of claim 1 wherein Alk is ethyl.

3. The method of claim 1 wherein said compound is 1-decylpiperidine hydrobromide.

4. The method of claim 1 wherein said compound is 1,10-bis(piperidino)decane dihydrobromide.

5. The method of claim 1 wherein said compound is 1,10-bis[4-(N,N-diethylcarbamoyl)piperidino]decane dihydrobromide.

6. The method of claim 1 wherein said compound is 1-decyl-3-(N,N-diethylcarbamoyl)piperidine hydrobromide.

7. The method of claim 1 wherein said compound is 1,10-bis[3-(N,N-diethylcarbamoyl)piperidino]decane dihydrobromide.

8. The method of claim 1 wherein said compound is 1-hexyl-3-(N,N-diethylcarbamoyl)piperidine hydrobromide.

9. The method of claim 1 wherein said compound is 1,6-bis[3-(N,N-diethylcarbamoyl)piperidino]hexane dihydrobromide.

10. The method of claim 1 wherein said compound is 1,3-bis[3-(N,N-diethylcarbamoyl)piperidino]propane dihydrochloride.

11. The method of claim 1 wherein said compound is 1,2-bis[3-(N,N-diethylcarbamoyl)piperidino]ethane dihydrobromide.

12. The method of claim 1 wherein said compound is 1-decyl-3-(N,N-diethylcarbamoyl)pyridinium bromide.

13. The method of claim 1 wherein said compound is 1-decyl-3-(N,N-diethylcarbamoyl)-1,2,5,6-tetrahydropyridine hydrochloride.

14. The method of claim 1 wherein said compound is 1-decyl-3-(N-ethylcarbamoyl)piperidine hydrobromide.

15. The method of claim 1 wherein said compound is 1-decyl-3-(carbamoyl)piperidine hydrobromide.

16. The method of claim 1 wherein said compound is 1,10-bis[3-(N,N-dimethylcarbamoyl)piperidino]decane dihydrobromide.

17. The method of claim 1 wherein said compound is 1,4-xylylenebis[3-(N,N-diethylcarbamoyl)piperidine hydrobromide].

18. The method of claim 1 wherein said compound is 1-(p-methylbenzyl)-3-(N,N-diethylcarbamoyl)piperidine hydrobromide.

19. The method of claim 1 wherein said compound is 1,3-xylylenebis[3-(N,N-diethylcarbamoyl)piperidine hydrochloride].

20. The method of claim 1 wherein said compound is trans-1,4-bis[3-(N,N-diethylcarbamoyl)piperidino]-2-butene dihydrochloride.

21. The method of claim 1 wherein said compound is cis-1,4-bis[3-(N,N-diethylcarbamoyl)piperidino]-2-butene dihydrobromide.

22. The method of claim 1 wherein the amount of said compound administered is from about 0.38 to about 3.8 mg/kg of said animal, every six hours.

* * * * *